(12) United States Patent
Hassler et al.

(10) Patent No.: US 7,257,996 B2
(45) Date of Patent: Aug. 21, 2007

(54) DEVICE AND METHOD FOR A QUALITY TEST OF A BODY

(75) Inventors: Ulf Hassler, Heilsbronn (DE); Peter Schmitt, Erlangen (DE); Guenther Kostka, Erlangen (DE)

(73) Assignee: Fraunhofer-Gesellschaft zur Foerderung der angewandten Forschung e.V. (DE)

( * ) Notice: Subject to any disclaimer, the term of this patent is extended or adjusted under 35 U.S.C. 154(b) by 116 days.

(21) Appl. No.: 11/197,656

(22) Filed: Aug. 4, 2005

(65) Prior Publication Data

US 2005/0286046 A1   Dec. 29, 2005

Related U.S. Application Data

(62) Division of application No. 10/433,994, filed on Oct. 23, 2003, now Pat. No. 7,088,442.

(51) Int. Cl.
*G01M 17/02* (2006.01)
(52) U.S. Cl. ........................................................ 73/146
(58) Field of Classification Search .................. 73/146; 378/61; 324/240
See application file for complete search history.

(56) References Cited

U.S. PATENT DOCUMENTS

| | | | | |
|---|---|---|---|---|
| 4,516,068 A | * | 5/1985 | Hawkinson et al. ......... | 324/558 |
| 4,934,184 A | * | 6/1990 | Tsuji ............................ | 73/146 |
| 5,060,173 A | * | 10/1991 | Tsuji ............................ | 702/35 |
| 5,060,250 A | * | 10/1991 | Kwee et al. .................. | 378/61 |
| 5,283,642 A | | 2/1994 | Sarr | |
| 5,455,870 A | | 10/1995 | Sepai et al. | |
| 5,825,670 A | | 10/1998 | Chernoff et al. | |
| 6,005,388 A | * | 12/1999 | Kaefer-Hoffmann et al. .... | 324/240 |
| 6,028,673 A | | 2/2000 | Nagasaki et al. | |
| 6,050,136 A | * | 4/2000 | Hawkinson et al. .......... | 73/146 |
| 6,119,514 A | * | 9/2000 | Piacente et al. .............. | 73/146 |
| 6,568,258 B1 | * | 5/2003 | Delmoro et al. .............. | 73/146 |
| 7,012,701 B2 | * | 3/2006 | Hassler et al. .............. | 356/601 |
| 7,088,442 B2 | * | 8/2006 | Hassler et al. ........... | 356/237.1 |

FOREIGN PATENT DOCUMENTS

| | | |
|---|---|---|
| DE | 38 27 696 C2 | 7/1992 |
| DE | 196 08 528 A1 | 9/1997 |
| DE | 198 49 793 C1 | 3/2000 |
| EP | 0 026 621 | 4/1981 |
| WO | WO 00/25088 | 5/2000 |

* cited by examiner

*Primary Examiner*—Andre J. Allen
(74) *Attorney, Agent, or Firm*—Beyer Weaver LLP

(57) ABSTRACT

A surface of a body includes a structure bounded by edges and a substantially edge-free unevenness. The structure is considered a quality impairment and the unevenness a potential quality impairment. A device includes a means for generating a height representation of the surface including the structure and the unevenness. A means for calculating a variation representation calculates the variation for every point of the height so that a high variation is obtained at a boundary of the structure and a low variation is obtained at a boundary of the unevenness. A means for detecting regions that potentially affect quality detects when a variation magnitude is smaller than a predetermined variation threshold value. These regions are examined to exclude uncritical regions and to determine the actual number of regions that affect quality. Quality control is performed on vehicle tires having structures such as inscriptions, and which also have bulges or constrictions that are substantially edge-free and uneven.

18 Claims, 3 Drawing Sheets

DEVICE AND METHOD FOR A QUALITY TEST OF A BODY

This application is a divisional of U.S. patent application Ser. No. 10/433,994, filed Oct. 23, 2003 now U.S. Pat. No. 7,088,442, entitled "Device and Method for A Quality Test Of A Body."

FIELD OF THE INVENTION

The present invention relates to industrial quality control performed on products with structured surfaces regarding the testing for defects of fabrication, and in particular to a device and a method for quality testing a body having a surface comprising a structuring limited by edges and a substantially edge-free unevenness.

BACKGROUND OF THE INVENTION AND PRIOR ART

In industrial quality control performed on products with surfaces comprising low-scale structured (relief-like) surfaces with regard to verification for defects fabrica-tion reflected by a specific anomaly of the shaping of the surface, contactless real-time measuring methods may be employed. Particularly in characterizing vehicle tires with regard to side or height wobble it is essential to recognize bulges or constrictions, on the one hand, and inscriptions and/or markings applied to the tires, on the other hand, so that they do not interfere with characterizing the vehicle tire.

The particular difficulty in detecting side or height wobble is the fact that raised, relief-like graphic characters or markings have been applied, as a rule simultaneously, on the areas to be tested, and that the anomaly structure is situated at the same height interval as the writing or at a lower height interval than same, it being possible that the tire surface to be tested additionally has a torus-shaped curvature.

As a consequence, correct measuring of the anomaly of height is distorted or, in many cases, even prevented by the presence of the structures of writing.

The production of vehicle tires may give rise to defects of fabrication in the inner structure which significantly influence the mechanical properties and therefore the operating behavior. It is necessary to discard any such products. In vehicle tires, such production defects may occur on the side faces or running treads, and typically become apparent in the form of deviations from a radially symmetric surface. The extensions of such imperfections are generally higher than the constructive structures which are present on the surface at the same time, such as relieves of writing or marking.

So far, mainly capacitive measuring methods have been employed for this test assignment in the field of industry, which, however, can only provide an insufficient testing depth for the reasons laid down below. While the surface is moving, i.e. while the tire is rotating, a change in the distance between the measuring electrode and the tire surface is determined by means of a change in the capacity of a measuring sensor. The distance lies in its relatively coarse lateral spatial resolution due to its geometry, which implies that only a small number of tracks per width of the testing range may be suitable for testing. The measurement signal contains no sufficient information on the precise course of a deflection in height, so that any short-range structures (relief or bulges/constrictions) cannot be differentiated and blanked out for further calculation.

In addition, certain tire manufacturers employ tactile (contacting) measuring methods, which, however, place certain requirements upon the geometry of the objects to be measured. The limitation is that on the surface to be examined, an explicit track to be measured must be provided which must not comprise any constructive structures, and the minimum width of which must include the geometry of the measuring sensor and potential irregularities in the concentricity during measuring. Under these circumstances, the measuring method is capable of determining relatively reliable measured values. However, due to the geometric limitations and the current tendency, conflicting therewith, to produce very narrow tire side flanks (tires with a small cross-section), it does not provide a satisfactory measuring method for general use.

A known method for measuring surface contours is optical triangulation. It includes focusing a light beam (generally a laser beam) onto the surface to be measured, and optically imaging the diffusely reflected radiation onto a sensor with a plurality of picture elements (pixels). If the geometry between the camera and the light beam remains unchanged, the change in the spatial position of the light intersection point on the object to be measured along the beam may be determined from a shift of the point of light reflected on the sensor area. Such a measurement is initially performed point by point. If a whole region is to be tested, the object under test is moved along beneath the triangulator measuring arrangement, and the measured values are recorded in a fast sequence, so that a narrow, annular track on the tire side face is detected.

With the increasing availability of high-performance laser light sources and optical sensors, bulge testing systems on the basis of laser triangulation have recently been offered. These systems are capable of capturing a specific track to be measured on the tire surface at a high spatial resolution, and to evaluate same with regard to potential shape anomalies. However, since these methods are not able to reliably recognize constructive structures of writing, the height of the shape anomalies is distorted by the height of the regular structures of writing. This is added to by the problem that the maximum amplitude of any occurring shape anomalies is not necessarily situated on the selected track to be measured.

A known derivative of the described triangulation which is also known includes sampling the surface by means of fan beam and area sensor (light section method). The height-related information may be determined along the measuring line on the surface by means of the light stroke projected onto the sensor (line of intersection between the fan beam and the object surface). By moving the object, the height-related information along this line is recorded row by row and subsequently combined to form a complete 2D height image comprising the respective height-related information in each image point. With sufficient resolution of the measurement in terms of space and time, the data set thus produced contains the height-related information derived from an entire surface region, including the structures of defects and writing and/or marking. However, since structures of writing and defects are situated in the same range of height, and since these structures are situated on a surface which is strongly curved in relation to these structures, it is not possible—even by means of the height images thus acquired—to achieve a secure differentiation between the respective relief structures in a simple manner without special data processing methods.

WO 00/25088 discloses methods and apparatus for determining points of unevenness in a domed surface, such as a tire side wall, using band-pass filtering. In particular, a three-dimensional surface representation of the tire side wall is created. Hereupon, the doming is extracted from the three-dimensional representation of the surface, and the edges of the structuring, such as of a writing or of markings, are smoothened to obtain a domeless representation of the domed surface. The surface now contains the potentially present unevenness, such as a constriction or a bulge on the tire side wall, but the edges of the inscription are now smoothened. Subsequently, the domeless representation is compared to a threshold so as to determine two-dimensional regions of the domeless representation which have a predetermined relation to the threshold value. Eventually, the areas of the determined regions are evaluated, wherein a region is detected to be an unevenness if its surface area is larger than a predetermined surface area. The relief-like structures of writing on the tires no longer play a role in evaluating the areas, since the edges of these inscriptions have been smoothened, and thus the heights of the inscriptions have been reduced such that they no longer exceed the threshold value at all, or such that they now have only a small area exceeding the threshold value. In the evaluation of the size of the areas exceeding the threshold value, these small areas may readily be distinguished from those areas which are due to bulges or constrictions. For extracting the surface and for smoothing the edges, a band pass filter is preferably used which has an upper and a lower cut-off frequency, the lower cut-off frequency being set such that the doming is suppressed, and wherein the upper cut-off frequency is set such that the edges are smoothened, whereas the points of unevenness in the form of bulges or constrictions substantially are not adversely affected.

Although, this method already brings substantial advantages compared to one-dimensionally working measurement methods, also here certain restrictions regarding testing capability exist, in particular regarding the maximum admissible height extension of the constructive structures, i.e. the structurings restricted by edges on the device under test. For a secure defect detection it needs to be guaranteed that the writing structures have at most the same height as the defect structures to be detected. Not rarely is it the case that a writing, i.e. a target structuring limited by edges is substantially higher than the defect to be determined in the form of bulges or constrictions. In the identification of substantially smaller defect structures than writing structures and also for the case that the writing structures are, however, present in the same height region but clearly expanded laterally, no secure difference between edgeless unevennesses and structurings limited by edges is possible any more. As the structurings are to be blanked out by low-pass filters, a secure blanking out is only guaranteed, when the structuring is not too high and not too large. If, however, a structuring which is too high or too large, respectively, is smoothed it becomes an artificially generated substantially edge-free unevenness after the low-pass filtering which may wrongly be seen as a bulge. If the structurings have a negative height extension, as it may for example occur by a stamp which is pressed into the tire surface, then this stamp may wrongly be seen as a constriction as it does not have any sharp edges anymore after low-pass filtering, has, however, not been suppressed so strong in order for its depth to be smaller than the critical depth predetermined for constrictions.

SUMMARY OF THE INVENTION

It is the object of the present invention to provide an improved device and an improved method for the quality testing of a body having a surface comprising a structuring bounded by edges and a substantially edge-free unevenness.

In accordance with a first aspect of the invention, this object is achieved by an apparatus for quality testing a body having a surface comprising a structuring bounded by edges and a substantially edge-free unevenness, wherein the structuring does not constitute a quality impairment, and wherein the unevenness constitutes a potential quality impairment, comprising: means for generating a height representation of the surface, wherein the height representation of the surface includes the structuring and the unevenness; means for calculating a variation representation from the height representation, wherein the variation representation includes variations of a height representation, so that at a boundary of the structuring a high variation is obtained, wherein at a boundary of the unevenness a low variation is obtained; and means for detecting regions of the height representation comprising a variation whose magnitude is smaller than a predetermined variation threshold value, wherein the variation threshold value is lower than the high variation und greater than the low variation, so that potentially quality-affecting regions are obtained.

In accordance with a second aspect of the invention, this object is achieved by a method for quality testing a body having a surface comprising a structuring bounded by edges and a substantially edge-free unevenness, wherein the structuring does not constitute any quality impairment, and wherein the unevenness constitutes a potential quality impairment, comprising the following steps: generating a height representation of the surface, wherein the height representation of the surface includes the structuring and the unevenness; calculating a variation representation from the height representation, wherein the variation representation includes variations of the height representation, so that at a boundary of the structuring a high variation is obtained, wherein at a boundary of the unevenness a low variation is obtained; and detecting of regions of the height representation comprising a variation whose magnitude is smaller than a predetermined variation threshold value, wherein the variation threshold value is lower than the high variation und greater than the low variation, so that potentially quality-affecting regions are obtained.

In accordance with a third aspect of the invention, this object is achieved by a method for positioning a defective location of a tire at a predetermined rotation position of a mechanical rotation axis, at which the tire is mounted, comprising the following steps: detecting a defective location of the tire by determining coordinates of the defective location, wherein the tire is turned around its mechanical rotation axis; determining rotation coordinates of the tire before, after or during the rotation of the tire around the mechanical rotation axis in the step of detecting, so that a direct relation between coordinates of the defective location and the determined rotation coordinates is present; and turning the tire around the mechanical rotation axis over an angular range which depends on the rotation coordinates of the tire and the coordinates of the defective location, so that the defective location of the tire is arranged at the predetermined rotation position of the mechanical rotation axis.

In accordance with a fourth aspect of the invention, this object is achieved by an apparatus for positioning a defective location of a tire at a predetermined rotation position of a mechanical rotation axis, at which the tire is mounted, comprising: means for detecting a defective location of the tire by determining coordinates of the defective location, wherein the tire is turned around the mechanical rotation axis; means for detecting rotation coordinates of the tire before, after or during the rotation of the tire around the mechanical rotation axis, so that a direct relation between coordinates of the defective location and the determined rotation coordinates is present; and means for turning the tire around the mechanical rotation axis across an angular range which depends on the rotation coordinates of the tire and the coordinates of the defective location, so that the defective location of the tire is arranged at the predetermined rotation position of the mechanical rotation axis.

The present invention is based on the findings that a substantial improvement in the quality testing is achieved when present target structurings, appearing as sharp edges, are not smoothed in order to suppress them, but that the edge characteristic is directly used to detect and mark the structurings as target structurings, so that these structurings may from the beginning be determined as not having defect zones. In contrast to the known method in which the target structurings were smoothed, hoping that they would be suppressed so far that they do not appear in the detection of bulges or constrictions, according to the invention the opposite way is taken. The attempt is not being made anymore to suppress the target structurings, but the target structurings are detected when examining the surface of the body regarding potential defect zones and declared to be target structures. To this end, a height representation of the surface of the body to be examined is generated, wherein the height representation still includes the structuring and the unevenness. Hereupon, a variation representation is calculated from the height representation, wherein the variation representation includes variations of the height representation associated with the points, at points of the height representation, so that at a boundary of the structuring limited by edges a high variation is obtained, while at a boundary the unevenness will obtain a low variation. Finally, areas of the height representation are detected, which comprises a variation which is smaller regarding its magnitude than a predetermined variation threshold value, and whose height or depth is larger than a predetermined detection threshold value, to obtain potentially quality-affecting regions.

As structurings bounded by edges comprise a high variation due to the sharp edges at the outer bounding, they are detected as non-quality-affecting regions in the inventive threshold value decision and therefore deliberately excluded.

One advantage of the present invention is that now no restrictions regarding the size and the height of the structurings or in other words regarding the height and the size of the deficiencies to be detected of the body are present which appear as edge-free unevennesses.

It is a further advantage of the present invention that due to the secure detection defect detections are excluded, i.e. no bodies are classified as defective anymore which are okay or basically no bodies are classified as okay anymore which are defective, respectively.

It is a further advantage of the present invention that the same thus contributes to a favorable final price of the body, as less defect detections take place and a manual final control may be completely omitted, or, if a manual final control takes place anyway, this final control may be performed by far less personnel, as due to the secure detection less control effort is present.

BRIEF DESCRIPTION OF THE DRAWINGS

In the following, preferred embodiments of the present invention are explained in more detail with reference to the accompanying drawings, in which.

DETAILED DESCRIPTION OF PREFERRED EMBODIMENTS

Figure 1:
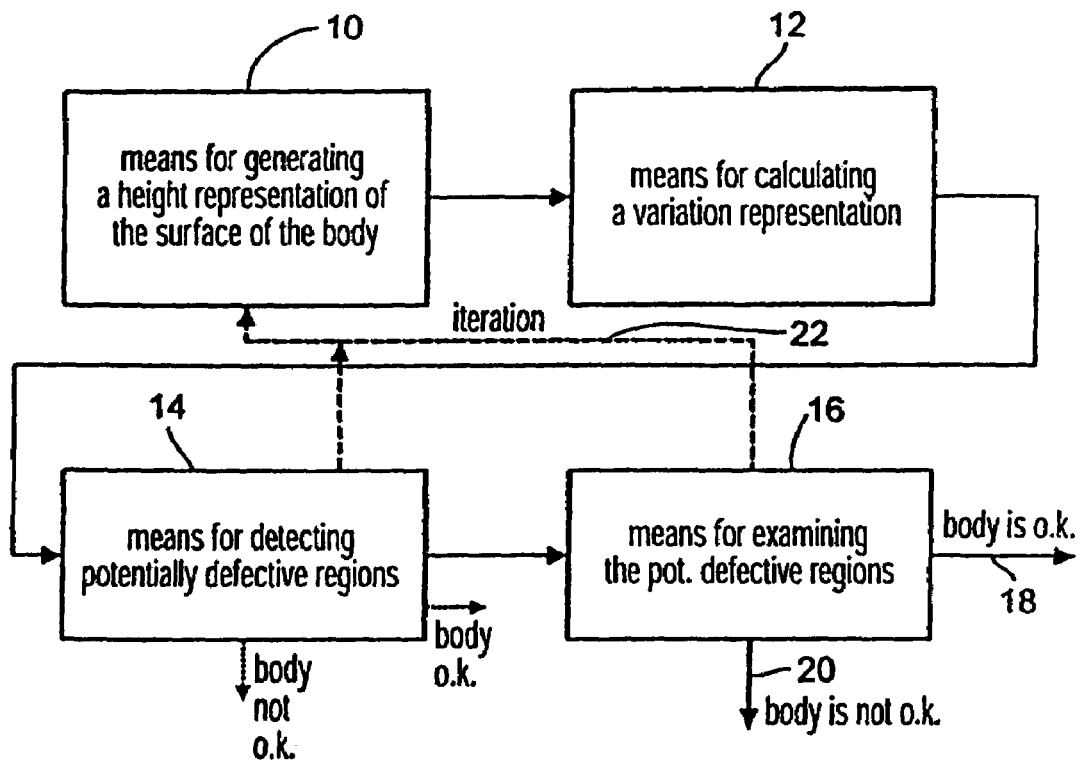
FIG. 1 shows a block diagram of an inventive device for quality testing a body having a surface.

FIG. 1 shows a block diagram of an inventive device for quality testing a body having a surface comprising a structuring bounded by edges and a substantially edge-free unevenness. Preferably, the inventive device is used for the quality testing of vehicle tires. In this case, the structurings bounded by edges include inscriptions, company emblems, which are raised over the surface of the tire, or stamps and the like, i.e. structurings which are as it were present below the surface of the vehicle tire, i.e. depressions bounded by edges. The substantially edge-free unevennesses are for example bulges or constrictions. It is known that a bulge with a certain form indicates a damage within the tire. The same is true for constrictions, i.e. depressions in the tire surface. Such disruptions of the surface of the tire caused by deficiencies of the body have no sharp edges in principle. Also if certain bulges or constrictions do for example not indicate functional defects of the tire due to their position on the tire or regarding their shape and height or depth, respectively, they may anyway be undesired, as they affect the overall optical impression of the tire, which is as important for many customers as the technical function of the tire or, with certain customer classes, even more important.

First of all, the inventive device includes a means for generating a height representation of the surface, wherein the height representation of the surface includes the structuring and the unevenness. If the inventive method is not applied to a domed surface, as it is for example present in a tire side flank, but if the inventive method is used for quality testing any surface, which may for example be even, then an image of the surface is made by the means for generating a height representation of the surface. The two-dimensionally arranged pixels of the surface result in a gray level image of the surface regarding their color information. Each gray level would therefore illustrate a certain height e.g. regarding an absolute reference point or regarding a mean height of the surface, so that negative height values e.g. by light gray color tones are labeled, while positive height values are illustrated by dark gray colors.

The means 10 for generating a height representation of the surface of the body is coupled to a means 12 for calculating a variation representation from the height representation, wherein the variation representation, at points of the height representation, includes variations of the height representation associated with the points, so that at a boundary of the structuring a high variation is obtained, while at a boundary of the unevenness a low variation is obtained. A sharp edge will manifest itself by a fast change of gray tones when the example of the gray level image is maintained, while the edge-free unevenness is characterized by a slow change of the gray tones from one pixel to the next. The variation representation therefore as it were illustrates the first derivative of the height representation. With two-dimensionally regarded surfaces, a derivative in the x direction and a derivative in the y direction will by required to this end. Thus, the variation representation may include two gradients for each point.

It is to be noted here, that the term "gradient" designates a vector whose magnitude is equal to the inclination value, and whose direction is equal to the direction of the inclination. The term "variation", however, only includes the magnitude of the gradient vector, is therefore a scalar value and is for example calculated from the sum of the squares of the difference of neighbored picture points. Regarding the present invention, the term "variation" is to be understood so that it also includes a gradient, and in particular any value providing information regarding a height difference between neighbored pixels. The variation of one pixel is for example calculated from the sum of the squares of the difference between the considered pixel for which the variation is calculated and any e.g. eight neighbored pixels. Obviously, also other calculation methods are conceivable, like e.g. the consideration of less than eight, like e. g. four, neighbored pixels etc. The variation only needs to indicate somehow whether a change of height from one pixel to another pixel is present.

It became clear, however, that it is sufficient to generate gradient information to the effect that it is known that at one pixel a high deviation to the next pixel is present, independent of the fact whether this deviation occurs in the x- or the y-direction. The variation representation may simply be generated by the fact that e. g. a number is associated with every gray level and that the gray level numbers of neighbored pixels are subtracted, wherein the difference is then a measure for the gradient. For summarizing the gradients in the x- and y-direction, for example the sum of the obtained differences could be added up.

Alternatively, also only a two-stage gradient representation method might be used in which it is determined that it is indicated that here a significant gradient is present when the difference is above a threshold value, while when the difference between the gray level numbers of two neighbored pixels is below a gradient threshold value no deviation to be considered is present. Alternatively, this decision may not only be performed in two stages but may be quantized into any number of stages, wherein the smallest quantizing is obviously given by the available gray levels.

The means 12 for calculating the variation representation is again coupled to a means 14 for detecting potentially defective regions. The means 14 for detecting regions of the height representation comprising a gradient which is smaller regarding its magnitude than a predetermined variation threshold value, and whose height is larger than a detection threshold value, serves for obtaining potentially quality-affecting regions from the variation representation. As it is known that structurings, like e.g. inscriptions etc., are not quality-affecting, only those regions in the variation representation or height representation, respectively, are detected which are surrounded by gradient values smaller than a variation threshold value. In addition, in the means 14 for detecting potentially defective regions a detection threshold value is used which considers the fact that not all elevations or depressions, respectively, i.e. any possibly present bulges or constrictions, are critical, as the critical bulges/constrictions distinguish themselves by a height deviation from the non-affected tire surface. If the height of a bulge or a constriction is so small that it may only go back to an unevenness of the rubber, which is serious neither optically nor constructively, then also this region is not detected as potentially quality-affecting, although it has a low gradient.

In principle, the inventive quality testing of the body might already end with the means 14, as already here a statement about the quality of the vehicle tire may be made. If a potentially quality-affecting region, i.e. a potentially defective region, has been detected, one output might be that the body, e.g. the tire, is sorted out and for example subjected to a manual post-control. When the means 14 for detecting regions has, however, not detected any potentially quality-affecting region, as on the tire only structurings bounded by edges were present, then the quality testing is also already ended, as the tire is classified as "okay".

In order to keep the number of false out-sortings, i.e. the number of decisions, in which a functional tire is designated as defective, as low as possible, a preferred embodiment of the present invention includes a means 16 for examining the potentially quality-affecting regions of the height representations regarding height or depth of the region and/or the area of the region to sense an actually quality-affecting unevenness to then sort out the tire. In a preferred embodiment, therefore first of all a means 16 will make the decision whether the body is okay (branch 18) or whether the body is not okay (branch 20).

Figure 2:
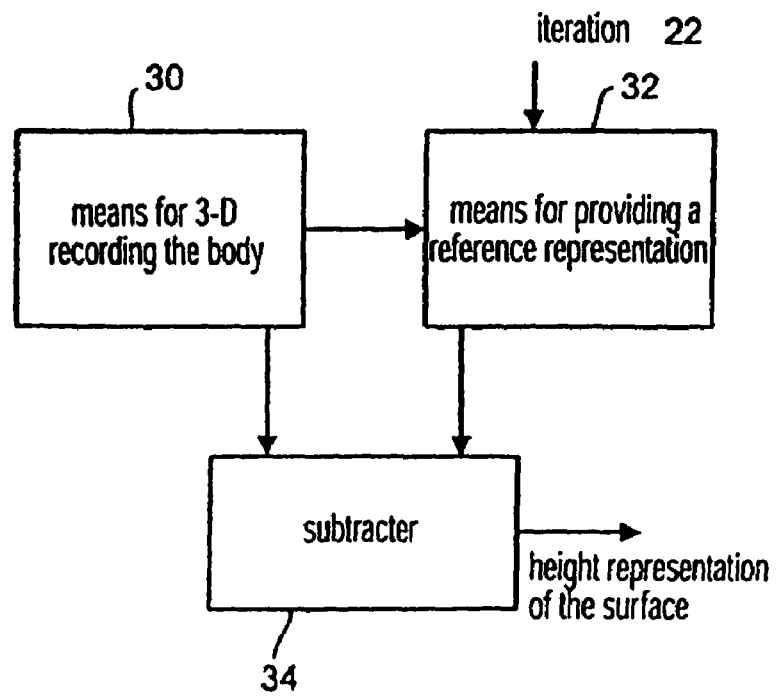
FIG. 2 shows an implementation of the means for generating a height representation of the surface of the body according to a preferred embodiment of the present invention.

In the preferred embodiment of the present invention, in which the means 16 for examining the regions detected as potentially defective by the means 14 is present, an iteration 22 may be performed so that the operation of the means for generating a height representation of the surface of the body designated with the reference numeral 10 in FIG. 1 is improved decisively, when the means 10 for generating a height representation of the surface of the body is implemented such that it includes the components shown in FIG. 2.

FIG. 2 shows a preferred embodiment of the means 10 for generating a height representation (FIG. 1). In particular, there is a problem regarding the examination of vehicle tires or generally the quality testing of bodies having curved surfaces, respectively, to the effect that the doming of the surface is not known from the beginning.

Thus, in such a case a simple height threshold value may not simply be used to sense the potentially defective regions. Instead, in the preferred embodiment of the present invention the proceedings are as follows. First of all, using a means 30 for a three-dimensional image of the body to be examined, a three-dimensional image is generated which includes in the case of a tire both the structurings bounded by edges and the substantially edge-free unevennesses. As the tire comprises a doming at its side flank, the representation generated by the means 30 also includes the doming of the tire and in addition, if present, a side wobble of the tire. In order to generate a height representation of the surface which only comprises the structuring and the unevenness, a reference representation is generated from the three-dimensional representation of the surface of the body, which does not comprise the target structurings and also not the edge-free unevennesses.

To this end, in one embodiment of the present invention a one-dimensional long-range non-linear filtering is performed, wherein the long-range filtering may be understood as a low-pass which affects the slow variations, like e.g. doming and wobble, which, however, suppresses the mean variations, like e.g. the variations caused by the unevenness and of course also the fast variations which are caused by the structuring. This reference representation generated by the means 32 is then subtracted from the original three-dimensional image using a subtractor 34, so that an planar height representation of the surface results which contains no more wobble and in particular no more doming of the surface. Then it may be operated using a simple height threshold value in the means 14 for detecting potentially defective regions, illustrated in FIG. 1.

As it was noted above, an iteration may take place to achieve a better height representation of the surface. If, for example, like in one preferred embodiment of the present invention, in the first pass of the iteration a long-range non-linear filtering for generating the reference height image (means 32 in FIG. 2) was performed, then in certain large writing structures remains of the writing structures may still remain. In the means 14 for detecting potentially defective regions (FIG. 1), an examination of the variation representation was already performed, however. If the examination of the variation representation is expanded to the effect that not only the potentially defective regions determined by the means 14 are searched but also the writing structures are determined, i.e. when the gradient values are searched for above the threshold value, then the potentially defective regions and the writing structures to be detected additionally may simply be eliminated by the three-dimensional representation generated by the means 30. Thus, an incomplete three-dimensional representation of the body is obtained which only includes the doming and the side wobble. When this incomplete representation is then subtracted or filled again by analytical functions which are fitted to the remaining support locations of the incomplete regions, the structureless and the depressionless reference representation may be obtained completely without writing and depressions. After subtracting using the subtractor 34 only the edge-bounded structurings and the substantially edge-free unevennesses remain, without any interferences by a non 100%-suppression using the long-range filter having taken place, which is used in the first pass in means 32. In the following, the means 12, 14 and 16 may again work with the now, however, newly generated height representation to mark potentially defective regions again and to examine the potentially defective regions again. By a comparison of the result regarding the potentially defective regions or the regions actually determined as defective regions at the end of the second iteration with the corresponding results at the end of the first iteration it may be determined whether the iteration did in fact bring any changes. If the iteration did bring changes, then the long-range filtering in block 32 was obviously not okay by 100 percent. If, however, between the two iteration results no substantial differences may be determined anymore, then the long-range filtering used for providing a reference representation was obviously effective when suppressing the depressions and edge structures. The iteration may be repeated until no substantial changes from iteration to iteration are determined anymore. As a decision criterion whether the iteration is to be terminated now a proportional or absolute change measure from one iteration to the next iteration may be used.

At this point it is to be noted that the means for providing a reference representation may thus perform a long-range low-pass filtering of the body to be examined in a first iteration. In the next iteration step, preferably a new filtering of the artifact-cleared height representation of the tire takes place after the detected structurings and the potentially defective regions have been removed from the three-dimensional representation of the body to obtain an incomplete representation and after the gaps of the incomplete representation were filled by interpolation. Thus, a reference representation of the tire without depressions and structurings is obtained so that the height representation of the surface becomes ever more plain and therefore ever better to be evaluated.

Alternatively, the reference representation may, however, also come from a data base. If, for example, the tires of a manufacturer are tested, the manufacturer might produce a tire without inscription which has accurately been tested manually regarding bulges and constrictions, to then measure these tires three-dimensionally, so that the three-dimensional representation of this "reference tire" may be used as a reference representation. This method will function well when the deviations from tire to tire are small. This method will also function efficiently when a long series of "identical" tires is to be examined.

In the following, reference is made to FIGS. 3a and 3b to illustrate a preferred embodiment of the inventive method for recognizing bulges/constrictions or generally substantially edge-free unevennesses on or in a surface of a body, respectively, for example of a tire. In a step 40 a data image of the tire is performed which is referred to in the following. Subsequently, in a step 42 a three-dimensional height image for example of the tire side wall is generated. In a step 44 an elimination of non-measurable regions is then performed by an interpolation between neighbored regions and a discarding of extreme height values for avoiding artifacts. Extreme height values for example result from measurement errors or also from point-like rubber spews which are present on new tires and which obviously do not represent a problem regarding the functioning or the optics of the tire.

Subsequently, as it has already been discussed regarding FIG. 1 or FIG. 2, respectively, in a step 46 a frequency height image is either provided to a data base externally or generated using the examined body. The reference height image should possibly be a structureless reference height image of the object doming which is preferably caused by a one-dimensional long-range non-linear filtering via a settable object region (angular region) in a tangential direction, i.e. in the peripheral direction, of the tire.

In a step 48, subsequently a planar tire height image is generated in which only bulges (constrictions) and writing but more side wobble and no doming is present anymore. This is achieved by a subtraction (means 34 of FIG. 2) of the reference representation from the three-dimensional representation of the body. To this end, as it is illustrated in a side-arrow 50 in FIG. 3a, the artifact-filtered three-dimensional height image is used. From the height representation generated by step 48, subsequently a variation representation is calculated (step 50), as it has been discussed above. Subsequently, potential defect zones are detected in a step 52. This is preferably done by determining and integrating zones within the height representation obtained by step 48, wherein zones are integrated whose height (illustrated by gray levels) is higher (or lower) than the detection threshold and whose variation is simultaneously below the variation threshold.

Optionally, these defect regions may still be processed with a non-linear two-dimensional filter to eliminate artifacts or minor defect regions already at this point. Therefore, regions are detected as potentially defective regions, which raise relatively slow from the tire or which depress into the tire, respectively, and which have a certain height. In order to give orders of magnitude it is to be noted that tires are examined accurately, such that already bulges or constrictions, respectively, are to be detected whose height above the surface or whose depth below the surface, respectively, lies in the range of 0.3 mm. Typically, bulges or constrictions are thought of as critical whose height or depth, respectively, is 0.6 mm or more. By the detection threshold used in step 52 therefore the sensitivity of the detection may be set. If the detection threshold is set very high, only relatively few potentially quality-affecting regions are detected, while when the detection threshold is set very low a plurality of potentially quality-affecting defects is generated. It is to be noted that the detection threshold may also be set to zero so that the inventive concept is merely degraded to a gradient detection. Then, all regions of the surface of the tire are detected which comprise a gradient below a certain value. The potentially quality-affecting zones are then any zones of the tire on which no writing or structuring, respectively, with sharp edges is present. In this view it is assumed that the regions of writing are not quality-affecting, while all other regions of the tire having a certain gradient may be quality-affecting. It is to be noted, that planar tire areas comprise no gradient, so that these are not detected as potentially quality-affecting.

At this point it is to be noted that in step 52 of a pixelwise processing which took place in the steps before step 52, a change is made to a zonewise processing. In a predetermined embodiment of the present invention regarding data processing at the output of step 52 no pixel representation is present anymore but a list of potentially defective regions which may, however, be uniquely associated with the original three-dimensional representation of the tire by its characteristics and coordinates. At the end of the method, when one of the regions listed in the list of potentially quality-affecting regions is classified as quality-affecting, it may therefore be indicated at which location of the tire the quality impairment is present, so that a person performing a manual quality control is directly led to the problematic location at the tire.

Figure 3A:
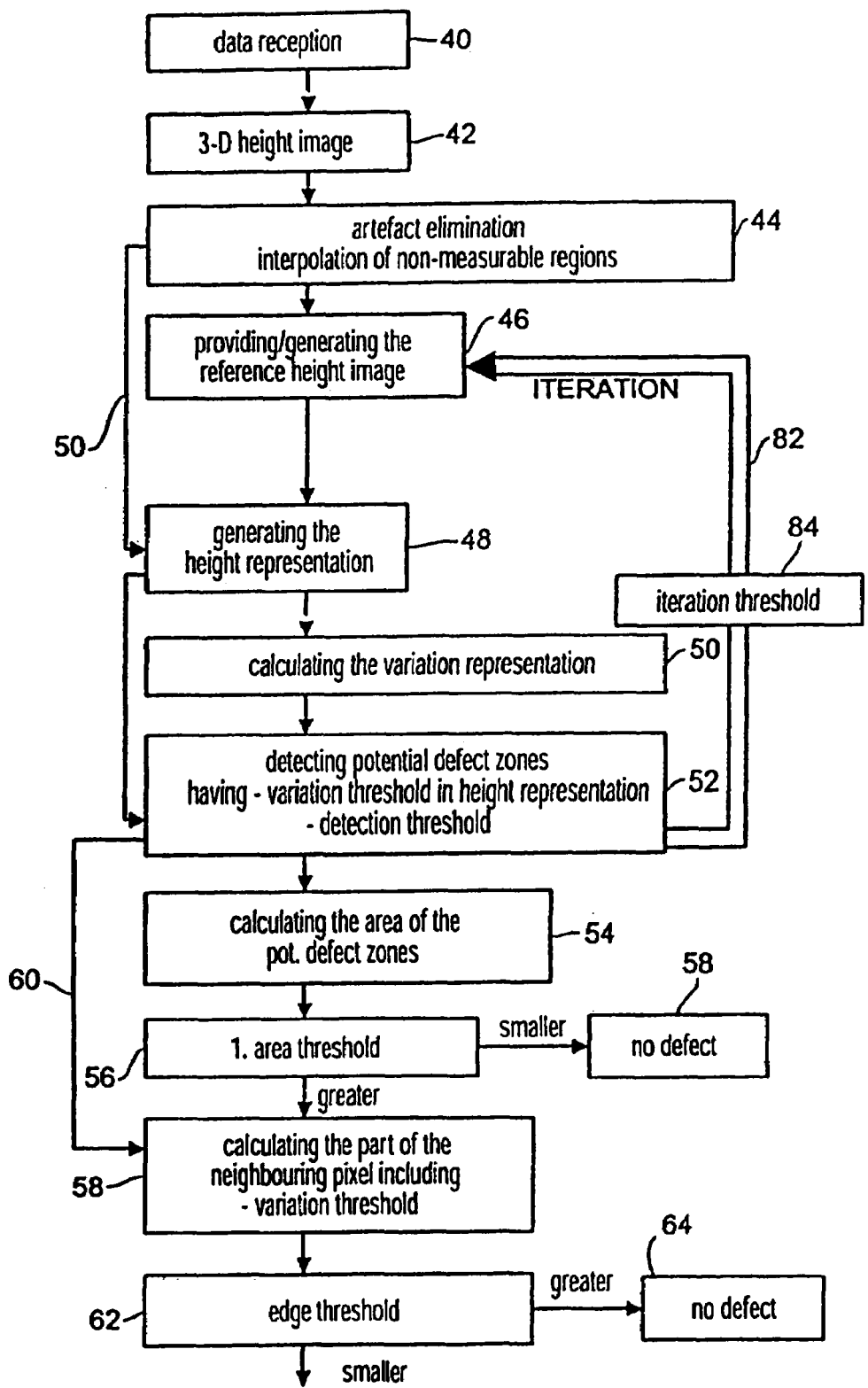
FIGS. 3a and 3b show an algorithm for quality testing a body according to a preferred embodiment of the present invention.
Figure 3B:
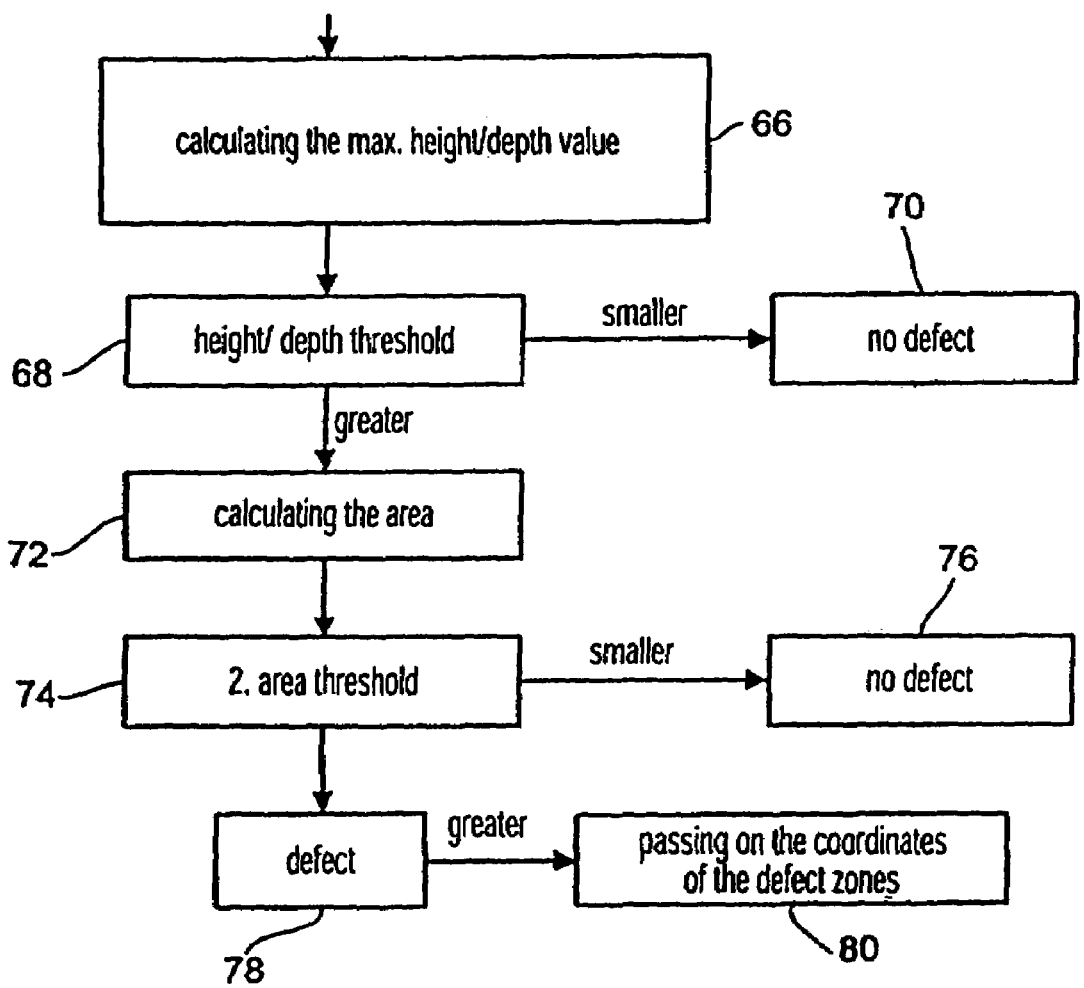

In the preferred embodiment of the present invention illustrated in FIG. 3a, in a step 54 an area calculation of the zones obtained by step 52 is performed, which are potential defect zones. In a step 56 the calculated areas are compared to a predetermined first area threshold. If it is determined that the area of a potential defect zone is smaller than the area threshold, this means that the defect zone is uncritical due to its small extension and that in this potential defect zone therefore no defect is present (58). If it is determined, however, that the area of a potential defect zone is larger than the area threshold, then this defect zone is further kept on the list of potential defect zones. The potential defect zone for which it was determined that same is unproblematic, is, however, eliminated from the list of potentially quality-affecting zones.

In a step 58 a further examination of the still remaining potential defect zones is performed. In particular, the proportional part of the neighboring pixels of the potential defect zones which were either calculated in step 52 or which still remained after step 56 is calculated, which comprise a high variation, i.e. a high gradient. To this end, the variation representation of step 50 is used, as it is illustrated by an arrow 60. For zones whose proportional part of neighboring pixels having a high variation is above a so-called edge threshold (step 62) are still identified as a structuring and classified as non-defective (64). If, however, the proportional part of the neighboring pixels of the respective zone is smaller than the predetermined edge threshold used in block 62, it may be assumed that here no structuring bounded by edges is present and that the respective region is still potentially quality-affecting.

The regions discarded by the comparison with the edge threshold in block 62 are, for example, such regions which do indeed have sharply delimited boundary but which are not fully flat within the boundary, that is to say which have a variation of zero, and which additionally have, within the sharp delimitation, a depression or elevation ascending gently and descending gently. Tire stampings may have such a structure. By examining the neighboring pixels of the region it may be ascertained whether there was a high variation immediately adjacent, so that, despite the fact that such a region has been classified as potentially defective in the examination in the means 52, same is still an uncritical target structuring. The percentage, that is to say the edge threshold, which becomes adjustable between 0 and 100%, will preferably be in a range between 80 and 100%, it being possible, however, to individually deal with the specific type of tire and/or the accuracy of the optical detection.

Of the remaining potential quality-impairing regions, the maximum height and/or depth value is calculated now in a step 66. Hereupon, a comparison operation of the values obtained with a height threshold or a depth threshold is performed in a block 68, it being possible for the height threshold and the depth threshold to have identical or different values, since the case may occur wherein bulges having a specific height are more critical than constrictions having the same height. If it is found out that the maximum height/depth of a region calculated has a higher value than the respective threshold, these respective regions are taken into account in further calculation. If it is found out, however, that the maximum heights/depths are smaller than the respective threshold, these regions are classified as undercritical. They do not present regions of defects (block 70), since, although they have passed some tests so far, their height/depth is too small for this unevenness to be critical in terms of the function of the tire and/or in terms of the function of the body undergoing a quality check by means of the surface examination.

Subsequently a calculation of the areas of the remaining regions is performed in a step 72, calculations of areas generally being performed by adding up the pixels in a region and then converting the magnification/reduction factors of the optics.

Eventually, the potentially quality-impairing regions which still remain after step 68 has been carried out, that is to say whose area has been calculated in step 72, are compared to a second area threshold, wherein, if their area value is smaller than the second area threshold, same are not classified as problematic, i.e. do not constitute a defect (block 76), whereas, if it is determined, in block 74, that the area of this region is larger than the second area threshold, this region is eventually classified as a region of defects (block 78). As has already been mentioned, the coordinates and extension of the region of defects, or, if several regions are problematic, of these several regions of defects, may be output in a step 80 to make it possible for a manual recheck to quickly find the respective locations.

It is to be noted here that for the purpose of a manual or any other verification of the found defect a device and a method for an automatic finding or positioning, respectively, of the defect may be used.

For this purpose a measurement system for determining the rotation position of the tire (preferably a rotator) is attached to the mechanical rotation axis of the tire and the measured values of the system are read in directly before and after or also during the recording of the height image of the tire into the measurement calculator via suitable interface. Thereby, the tire should not be unclamped or, if it is unclamped, be clamped into the same angular position again regarding the mechanical rotation axis, respectively.

Due to the obtained time synchronization and the thus obtained direct relationship between the coordinates of the height image and the measured angular values the angular position of the detected defect may be calculated and used for an exact automatic positioning of the tire.

In a preferred embodiment, the rotation of the tire axis may then be stopped via an electric signal at the control of the axis at a predetermined angular position of the test equipment and at a point of time pre-calculated due to the defect coordinates.

It is to be noted that for finding the defective location of the tire either the inventive method or also any other method may be used, like e.g. one of those described in the prior art. Preferably, the method works for automatically detecting the defective location.

For improving the height measuring accuracy, optionally the iteration described regarding FIGS. 1 and 2 may be performed by iteratively repeating the steps 46, 48, 50, 52 after the step 52, as it is indicated by an iteration arrow 82. To this end, in step 46 for providing/generating the reference height image only those object ranges are used which are not potentially quality-affecting and which are additionally no writing ranges, i.e. comprise a high gradient. The then remaining incomplete three-dimensional representation for example of the tire may be fitted and replaced by analytic (periodic or aperiodic) functions. Alternatively, the whole tire shape may be fitted analytically using the remaining object zones. Alternatively, an interpolation using cubic splines or similar methods may also be used.

The number of iterations to be performed depends on the desired measurement accuracy. A termination criterion may for example be defined such that the coefficients or the difference of the absolute height values of the domed tire form from subsequent iterations differentiate by less than a determined threshold, as it is illustrated by block 84 designated by "iteration threshold" in FIG. 3a.

At this point it is to be noted that the sequence of the individual threshold value decisions is random. In addition, in principle also a single area threshold would suffice. If, however, two area thresholds are used (block 56 and block 74), then also intermediate results may be obtained about the tire, i.e. whether it comprises bulges or constrictions, respectively, and whether the bulges are undercritical, i.e. that their area lies between the first and the second area threshold. Of course, the area threshold decision might, for example, take place before the edge threshold decision or before the height threshold decision (block 68). For minimizing the calculation effort it is preferred, however, to first perform the decisions using which a number as high as possible of the potentially quality-affecting areas are classified as non-critical, so that the list of the potentially quality affecting regions to be examined gradually become as small as possible as fast as possible. Alternatively, also the order of the threshold value decisions might be selected so that a defective zone is found as fast as possible, which leads to the fact that the tire is discarded. In this case it is not important whether further defect zones are present or whether further potential defective zones are present, respectively, as already one defective zone is sufficient to make the tire a defect tire.

Subsequently, an optical system is referred to which is preferably used for the present invention. A light fan beam (laser with specific aspherical refractive optics, 30 mW) is initially directed at the surface to be examined. The diffusely reflected radiation is projected onto a sensor face via a suitable lens system. The shape of the surface irradiated is calculated from the known geometry of the measuring arrangement from the position of the projected line on the sensor face.

The geometry of the arrangement of the light fan beam and the measuring camera as well as the pixel resolution of the camera determine the spatial resolution of the measurement in the lateral and vertical directions. The geometry is selected such that the tire region to be examined is imaged onto the sensor, i.e. a measuring region of 5 cm in the radial direction with a resolution of 0.5 mm, and such that a sufficient height resolution of about 75 µm is achieved at the same time in order to represent the structures of defects, which occur in a range of height $>=0.55$ mm, in a sufficiently accurate manner.

The spatial resolution of the measurement in the tangential direction is dependent on the image repetition rate of the image camera. The tangential spatial resolution is 1 mm. A tire must be tested within 1 sec. With an assumed diameter of the testing region of, for example, 60 cm, this results in a measuring rate of 1,900 Hz. Sensors specifically suitable for this test problem are manufactured by IVP (type MAPP 2500 PCI). By means of a programmable computer architecture integrated on the sensor chip, a column-by-column determination of the height-related information is performed, so that per sensor image captured, it is only the evaluation result that must be transmitted to the measuring computer in the form of a line.

The light source/camera arrangement which may be employed for the present invention may be the same, for example, as has been described in WO 00/25088. A suitable camera typically has a dust-proof housing, the measuring windows being kept free from dust by means of air cleaning. The height measuring region, which may be realized with such a light source/camera arrangement, in the z direction is 39 mm. The height resolution is 75 µm. The width of the measuring region on the tire flank is, for example, 80 mm.

What is claimed is:

1. An apparatus for positioning a defective location of a tire at a predetermined rotation position of a mechanical rotation axis, on which the tire is mounted, comprising:
    a defect location detector for detecting a defect location of the tire by determining coordinates of the defect location, wherein the tire is turned about the mechanical rotation axis;
    a rotation detector connected to the defect location detector for detecting angular rotation coordinates of the tire before, after or during the rotation of the tire about the mechanical rotation axis, so that a direct relation between the coordinates of the defect location and the detected angular rotation coordinates is present; and
    a turner connected to said rotation detector for turning the tire about the mechanical rotation axis across an angular range which depends on the angular rotation coordinates of the tire and the coordinates of the defect location, so that the defect location of the tire is arranged at the predetermined rotation position of the mechanical rotation axis.

2. The apparatus of claim 1, in which the tire has a surface comprising a structure bounded by edges and a substantially edge-free unevenness, wherein the structure does not constitute a quality impairment, and wherein the unevenness constitutes a potential quality impairment, the defect location detector comprising:
    a height representation generator for generating a height representation of the surface, wherein the height representation of the surface includes the structure and the unevenness;
    a calculator for calculating a variation representation from the height representation, wherein the variation representation includes variations of a height representation, so that at a boundary of the structure a high variation is obtained, wherein at a boundary of the unevenness a low variation is obtained; and
    a region detector for detecting regions of the height representation comprising a variation whose magnitude is smaller than a predetermined variation threshold value, wherein the variation threshold value is lower than the high variation and greater than the low variation, so that potentially quality-affecting regions are obtained.

3. The apparatus according to claim 2, wherein the region detector is arranged to obtain only such regions as potentially quality-affecting whose height is larger than a predetermined detection threshold value.

4. The apparatus according to claim 2, further comprising:
an examiner for examining the potentially quality-affecting regions of the height representation regarding a height or depth and/or area in order to detect a quality-affecting unevenness.

5. The apparatus according to claim 2, wherein the surface is torus-shaped and comprises a doming and, if applicable, a side wobble, wherein the means for generating a height representation of the surface comprises:
a generator for generating a three-dimensional representation of the surface;
a provider for providing a reference representation of the surface, wherein the reference representation reflects the surface without the structure and the unevenness; and
a subtracter for subtracting the reference representation from the three-dimensional representation to obtain a planar height representation of the surface of the body.

6. The apparatus according to claim 4, wherein the examiner comprises:
a filter for non-linear two-dimensional filtering of the potentially quality-affecting regions to detect artifacts or small regions as not being quality-affecting.

7. The apparatus according to claim 4, wherein the examiner is arranged to determine the areas of the potentially quality-affecting regions and to compare the determined areas to at least one predetermined area threshold, to classify the potentially quality-affecting ranges as not being quality-affecting, whose areas are smaller than the predetermined area threshold.

8. The apparatus according to claim 7, in which a predetermined area threshold for elevations and a predetermined area threshold for depressions is provided.

9. The apparatus according to claim 4, wherein the examiner is arranged to determine a proportional part of adjacent pixels for a potentially quality-affecting range, which comprises a variation which is in its magnitude larger or equal to the predetermined variation threshold value, and wherein the examiner is further arranged to compare the proportional part to a predetermined edge threshold value, wherein potentially quality-affecting regions with a proportional part larger than the edge threshold value are classified as not being quality-affecting.

10. The apparatus according to claim 4, wherein the examiner is further arranged to compare potentially quality-affecting regions to a predetermined height threshold value to classify the regions whose height is smaller than the predetermined height threshold value as not being quality-affecting regions.

11. The apparatus according to claim 4, wherein the examiner is arranged to calculate the areas of potentially quality-affecting regions and to classify the potentially quality-affecting regions as quality-affecting regions whose area is larger than a predetermined area threshold value.

12. The apparatus according to claim 5, wherein the provider for providing a reference representation is arranged to perform a long-range non-linear filtering of a three-dimensional representation of the body.

13. The apparatus according to claim 12, wherein the provider for providing a reference representation is arranged to eliminate in an iteration the potentially quality-affecting regions from the three-dimensional representation of the object, to obtain an incomplete three-dimensional representation and to interpolate the incomplete three-dimensional representation or to fit the same by an analytical function to obtain the reference representation of the surface.

14. The apparatus according to claim 2, wherein the height representation is an planar height representation.

15. The apparatus according to claim 2, wherein the height representation is a contour line of a track on the surface and wherein a potentially quality-affecting region is a section of the contour line.

16. The apparatus according to claim 2, wherein the structure comprises an inscription on the tire and the substantially edge-free unevenness includes a bulge or a constriction.

17. The apparatus according to claim 2, wherein the height representation generator for generating a height representation is further arranged to eliminate generated pixel artifacts in an image of the surface.

18. A method for positioning a defective location of a tire at a predetermined rotation position of a mechanical rotation axis, on which the tire is mourned, comprising the following steps:
detecting a defect location of the tire by determining coordinates of the defect location while the tire is turned around its mechanical rotation axis;
determining angular rotation coordinates of the tire before, after or during the rotation of the tire about the mechanical rotation axis during the step of detecting, so that a direct relation between the coordinates of the defect location and the determined angular rotation coordinates is present; and
turning the tire about the mechanical rotation axis over an angular range using the angular rotation coordinates of the tire and the coordinates of the defect location, so that the defect location of the tire is arranged at the predetermined rotation position of the mechanical rotation axis.

* * * * *